United States Patent
Bengtsson et al.

(10) Patent No.: US 10,293,109 B2
(45) Date of Patent: May 21, 2019

(54) ADAPTIVE SYSTEM FOR OPTIMIZING A DRUG DOSAGE REGIMEN OVER TIME

(75) Inventors: Henrik Bengtsson, Taastrup (DK); Anders Dejgaard, Hellerup (DK); Alan Moses, New Hope, PA (US)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 14/344,250

(22) PCT Filed: Sep. 11, 2012

(86) PCT No.: PCT/EP2012/067705
§ 371 (c)(1),
(2), (4) Date: Aug. 25, 2014

(87) PCT Pub. No.: WO2013/037754
PCT Pub. Date: Mar. 21, 2013

(65) Prior Publication Data
US 2014/0371682 A1    Dec. 18, 2014

Related U.S. Application Data (60) Provisional application No. 61/535,079, filed on Sep. 15, 2011.

(30) Foreign Application Priority Data

Sep. 13, 2011 (EP) .................................. 11180998

(51) Int. Cl.
*A61M 5/24* (2006.01)
*G06F 19/00* (2018.01)
*A61M 5/31* (2006.01)

(52) U.S. Cl.
CPC ............... *A61M 5/24* (2013.01); *G06F 19/00* (2013.01); *G06F 19/3468* (2013.01);
(Continued)

(58) Field of Classification Search
CPC ........ A61M 5/1723; A61M 2005/3125; A61M 2005/3126; A61M 2230/201; A61M 2205/52; G06F 19/3468; A61B 5/14532
See application file for complete search history.

(56) References Cited

U.S. PATENT DOCUMENTS

| 7,491,187 B2 | 2/2009 | Van Den Berghe et al. |
| 2005/0192494 A1* | 9/2005 | Ginsberg ...................... 600/365 |

(Continued)

FOREIGN PATENT DOCUMENTS

| EP | 1571582 A2 | 9/2005 |
| JP | H10-504729 A | 5/1998 |

(Continued)

OTHER PUBLICATIONS

Blonde L. et al,Patient-directed titration for achieving glycaemic goals using a once-daily basal insulin analogue: an assessment of two different fasting plasma glucose targets—the Titrate study, Journal :Diabetes, Obesity and Metabolism, Year 2009, vol. 11,pp. 623-631.

*Primary Examiner* — Nathan R Price
*Assistant Examiner* — Justin L Zamory
(74) *Attorney, Agent, or Firm* — Leon Y. Lum (57) ABSTRACT

A system for optimizing a patient's basal insulin dosage regimen over time, adapted to determine from blood glucose values whether and by how much to vary a patient's present recommended amount of the insulin-containing drug in order to maintain the patient's future blood glucose level measurements within a predefined range, and wherein a given blood glucose value is disregarded if no patient-actuated operation being indicative of the administration of a dose of an insulin containing drug has been detected in a pre-defined amount of time prior to the determination of the given blood glucose value.

12 Claims, 5 Drawing Sheets

(52) U.S. Cl.
 CPC ............ *A61M 2005/3125* (2013.01); *A61M 2005/3126* (2013.01); *A61M 2205/50* (2013.01); *A61M 2205/8206* (2013.01)

(56) References Cited

U.S. PATENT DOCUMENTS

| | | |
|---|---|---|
| 2005/0272640 A1 | 12/2005 | Doyle et al. |
| 2009/0253970 A1 | 10/2009 | Bashan et al. |
| 2009/0253973 A1 | 10/2009 | Bashan et al. |
| 2010/0016700 A1* | 1/2010 | Sieh .................. A61B 5/14532 600/365 |
| 2010/0331651 A1 | 12/2010 | Groll |
| 2011/0077493 A1 | 3/2011 | Shadforth et al. |
| 2011/0098548 A1 | 4/2011 | Budiman et al. |

FOREIGN PATENT DOCUMENTS

| | | |
|---|---|---|
| JP | 2003-079723 A | 3/2003 |
| JP | 2005-512689 A | 5/2005 |
| WO | 2004/084820 A2 | 10/2004 |
| WO | 2009/146119 A2 | 12/2009 |
| WO | 2009/146121 A2 | 12/2009 |
| WO | 2010/009382 A2 | 1/2010 |
| WO | 2010/056718 A2 | 5/2010 |
| WO | 2010/089304 A1 | 8/2010 |
| WO | 2010/089307 A1 | 8/2010 |
| WO | 2010/098927 A1 | 9/2010 |
| WO | 2010/098931 A1 | 9/2010 |
| WO | 2011/084801 A2 | 7/2011 |

\* cited by examiner

ADAPTIVE SYSTEM FOR OPTIMIZING A DRUG DOSAGE REGIMEN OVER TIME

The present invention generally relates to systems and methods allowing a patient to optimize a drug dosage regimen over time.

CROSS-REFERENCE TO RELATED APPLICATIONS

This application is a 35 U.S.C. § 371 National Stage application of International Application PCT/EP2012/067705 (published as WO 2013/037754), filed Sep. 11, 2012, which claimed priority of European Patent Application 11180998.4, filed Sep. 13, 2011; this application claims priority under 35 U.S.C. § 119 of U.S. Provisional Application 61/535,079; filed Sep. 15, 2011.

BACKGROUND OF THE INVENTION

In the disclosure of the present invention reference is mostly made to the treatment of diabetes by delivery of insulin, however, this is only an exemplary field of use for the present invention.

Type 2 diabetes is a progressive disease in which β-cell function deteriorates. Initiating therapy with oral agents is a reasonable approach to take with most patients, the exception being patients with extreme hyperglycemia (fasting plasma glucose >250 mg/dl). These patients require insulin to lower glucose levels. Otherwise, starting with oral therapy can be very effective, especially in patients with a short duration of diabetes and, thus, relatively adequate β-cell function. However, during the course of the decease many patients sooner or later will need therapy with insulin. When determining whether a patient should be put on insulin therapy, it is helpful to look to the guidelines for glycemic control. The American Diabetes Association (ADA) and American College of Endocrinology (ACE) publish goals for A1C, postprandial glucose, and fasting/pre-prandial glucose. Most patients who are unable to achieve these goals using oral agents are candidates for insulin therapy.

One type of initial insulin therapy for Type 2 diabetics is to use once-daily injections with a long-acting insulin such as Levemir® (insulin detemir) or Tresiba® (insulin degludec) from Novo Nordisk, often in combination with oral antidiabetic agents. However, to be successful, insulin therapy requires timely and appropriate titration of dosages. For example, in combination with oral antidiabetic agents it is recommended to initiate Levemir® treatment with once daily administration at a dose of 10 U or 0.1-0.2 U/kg. The dose of Levemir® should then be titrated based on individual patients' needs, e.g. based on average (3-7 measurements) self-measured pre-breakfast blood glucose (BG) values. For example, for a calculated value of >10.0 mmol/L it is recommended to adjust the Levemir® dose with +8 units, for a calculated value of 9.1-10.0 mmol/L it is recommended to adjust the Levemir® dose with +6 units, for a calculated value of 8.1-9.0 mmol/L it is recommended to adjust the Levemir® dose with +4 units, for a calculated value of 7.1-8.0 mmol/L it is recommended to adjust the Levemir® dose with +2 units, and for a calculated value of 6.1-7.0 mmol/L it is recommended to adjust the Levemir® dose with +2 units. If one BG measurement is 3.1-4.0 mmol/L it is recommended to adjust the Levemir® dose with −2 units, and if one BG measurement is <3.1 mmol/L it is recommended to adjust the Levemir® dose with −4 units. The calculation of the average pre-breakfast BG values as well as the resulting Levemir® dose adjustments may either be performed by the patient him/herself or by a doctor/nurse based on BG values supplied by the patient. As appears, such a regimen is both time-consuming as well as prone to mistakes. This said, self-titration regimens are considered to facilitate empowerment of patients, allowing them to become more involved in their treatment which may then result in improved glycaemic control.

Correspondingly, devices and systems have been provided in which recommendations are generated based on self-measured BG values by a pre-programmed algorithm, e.g. corresponding to the relatively simple titration regimen described above. Indeed, much more sophisticated algorithms can be implemented taking into account e.g. patient characteristics and other variable inputs, see e.g. US 2009/0253970. The algorithm may be in the form of software adapted to run on different platforms, e.g. PC, PDA or smartphone, or it may be impeded in a device such as a BG meter, see e.g. US 2010/0016700. EP 1 571 582 discloses methods in which BG values are used to calculate CIR and ISF values.

Although such automatically generated recommendations may be of great help to both medical staff and patients, the recommendations may be wrong if they are based on incorrect assumptions, especially that the patient follows the regimen as prescribed.

Having regard to the above, it is an object of the present invention to provide systems and methods supporting cost-effective optimization and control of patient self-titration of a medical regimen.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a system for optimizing a patient's basal insulin dosage regimen over time is provided, comprising a BG meter (BGM) for receiving a patient blood sample and generating a BG data set corresponding to a BG value of the patient blood sample (e.g. BG value and time), and memory means adapted to receive (a) data representing an initial basal insulin dosage regimen, and (b) BG data sets corresponding to a plurality of BG values as a function of time. The system further comprises a processor operatively connected to the memory means, the processor being programmed to determine from the BG data sets determined at a plurality of times whether and by how much to vary a component in the patient's present insulin dosage regimen (i.e. to provide a recommendation) in order to maintain the patient's future BG-level measurements within a predefined range, and output means for communicating to the patient the determined variation in the component in the patient's insulin dosage regimen. The processor is programmed to calculate a correction value representing, for blood glucose data sets determined at a plurality of times, the degree of deviation between determined and expected values. The calculated variation of the component is then reduced as a function of the calculated correction value, e.g. the higher the correction value the more the calculated recommendation (variation from a previous value) is reduced. In other words a safety factor has been incorporated.

As appears a two-step approach is provided as the system in this way is able to partly compensate for abnormal patterns and potential issues in the titration process by reducing the "aggressiveness" of the calculated titration which may otherwise result in hypoglycaemia and potential dangerous situations for the patient. The calculated recommendations and the calculated correction value may be logged separately and retrieved by a doctor, this providing a more detailed insight in the progress in the patients titration, e.g. a high correction value may explain why titration progress is slower than expected.

The "expected values" could be pre-set and/or calculated dynamically, e.g. a given predefined range for a mean value based on a number of previous determined values. The values will typically by BG values but could also include time values, e.g. time ranges within which BG values are expected to be determined.

The correction value could be based on a number of calculations, e.g. a calculated variance value or a value based on a scoring system, e.g. each BG value is given a score based upon its deviation from an expected pre-set value or a calculated mean value. In addition, a given BG data set corresponding to a BG value outside a predefined range or taken at a non-prescribed time may also result in the BG data set being disregarded when calculating the recommendation. The correction factor could also incorporate further factors, e.g. an additional safety factor chosen by the patient's doctor.

In a specific configuration the system may be in the form of a drug delivery assembly comprising (a) a drug delivery device comprising a drug reservoir or means for receiving a drug reservoir, an outlet for the drug, a drug expelling mechanism for expelling drug from the reservoir and out through the outlet, and (b) a cap device releasably mountable on the drug delivery device and adapted to cover the outlet in a mounted position, the cap device comprising the BGM, the memory means and the processor, and the output means. In this way a titration device can be provided in the form of a cap device which can be used in combination with either a pre-filled disposable or user-fillable durable drug delivery device, e.g. in pen form.

In a further specific configuration the system may be in the form of an assembly comprising a drug delivery device unit comprising a drug reservoir or means for receiving a drug reservoir, an outlet for the drug, a drug expelling mechanism for expelling drug from the reservoir and out through the outlet, the memory means and the processor, receiving means for receiving BG data from the BGM, and the output means. The BGM is then provided as a stand-alone unit comprising transmission means for transmitting BG data to the drug delivery device unit, e.g. wirelessly.

The system of the first aspect may further comprise detecting means for detecting when a patient-actuated operation is performed, the operation being indicative of the administration of a dose of an insulin containing drug, wherein the memory means is adapted to receive data representing detected patient-actuated operations as a function of time. The processor is further programmed to calculate a compliance value based on the detected patient-actuated operations compared to a pre-defined schedule for the patient-actuated operations, whereby the calculated variation of the component can be reduced as a function of a the compliance value. For example, each detected (as well as missing) operation may be scored based on the pre-defined schedule, this resulting in a combined score for a given period. The "worse" the score the less aggressive the titration will be.

The detection and compliance value feature could also be implemented to replace the above-disclosed correction value, i.e. a system is provided in which the calculated variation of the component is reduced merely as a function of the compliance value.

In a specific configuration the system may be in the form of a drug delivery assembly comprising a drug delivery device comprising a drug reservoir or means for receiving a drug reservoir, an outlet for the drug, and a drug expelling mechanism for expelling drug from the reservoir and out through the outlet, as well as a cap device releasably mountable on the drug delivery device and adapted to cover the outlet in a mounted position. The cap device comprises the BGM, the memory means and the processor, the output means, and the detecting means. The detection means is adapted to detect a cap-off event when the cap has been at least partially de-mounted from the drug delivery device for a pre-determined amount of time. As appears, the cap-off event is considered to represent the action of administration of a dose of an insulin containing drug.

In a further specific configuration the system may be in the form of a drug delivery assembly comprising a drug delivery device comprising a drug reservoir or means for receiving a drug reservoir, an outlet for the drug, a drug expelling mechanism which can be set to expel a desired dose of drug from the reservoir and out through the outlet when actuated, and means for detecting, storing and transmitting dose data representing the size of an expelled dose, as well as a cap device releasably mountable on the drug delivery device and adapted to cover the outlet in a mounted position. The cap device comprises the BGM, the memory means and the processor, the output means, and receiving means for receiving dose data from the drug delivery device. Drug delivery devices provided with electronic means for detecting the amount of actually expelled drug are known, see e.g. WO 08/037801. Such a device may be adapted to transmit data to a cap device, e.g. wirelessly, optically or via galvanic contacts. As appears, the event of expelling a dose of insulin is considered to represent the action of actual administration of a dose of an insulin containing drug. Alternatively, the cap device could be provided by a BGM unit having the additional features of the cap.

In a yet further specific configuration the system may be in the form of a drug delivery assembly comprising a drug delivery device comprising a drug reservoir or means for receiving a drug reservoir, an outlet for the drug, a drug expelling mechanism for expelling drug from the reservoir and out through the outlet, the BGM, the memory means, the processor, the output means, and the detecting means. In such an integrated system the detection means is adapted to detect when the drug expelling mechanism has been actuated. The system may further comprise a cap device releasably mountable on the drug delivery device and adapted to cover the outlet in a mounted position.

For any of the above systems a given BG data set may be disregarded by the processor if the given BG data set corresponds to a BG value outside a predefined range. Further, if the system comprises detection means adapted to detect e.g. a cap-off event when the cap has been at least partially de-mounted from the drug delivery device for a pre-determined amount of time, then the system can take into account that the patient has not used the drug delivery device in accordance with the regimen. For example, if the patient is supposed to take an amount of Levemir® at bed time, then failure to take off the cap e.g. in the time range 6:00-11:00 PM prior to determining a morning BG (e.g. in the time range 6:00-9:00 AM) would result in the algorithm disregarding the BG value when calculating a recommendation. If the cap does not comprise a real time clock then a time range relative to BG measurement could be defined.

As used herein, the term "insulin" is meant to encompass any drug-containing flowable medicine capable of being passed through a delivery means such as a cannula or hollow needle in a controlled manner, such as a liquid, solution, gel or fine suspension, and which has a BG controlling effect, e.g. human insulin and analogues thereof as well as non-insulins such as GLP-1 and analogues thereof. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
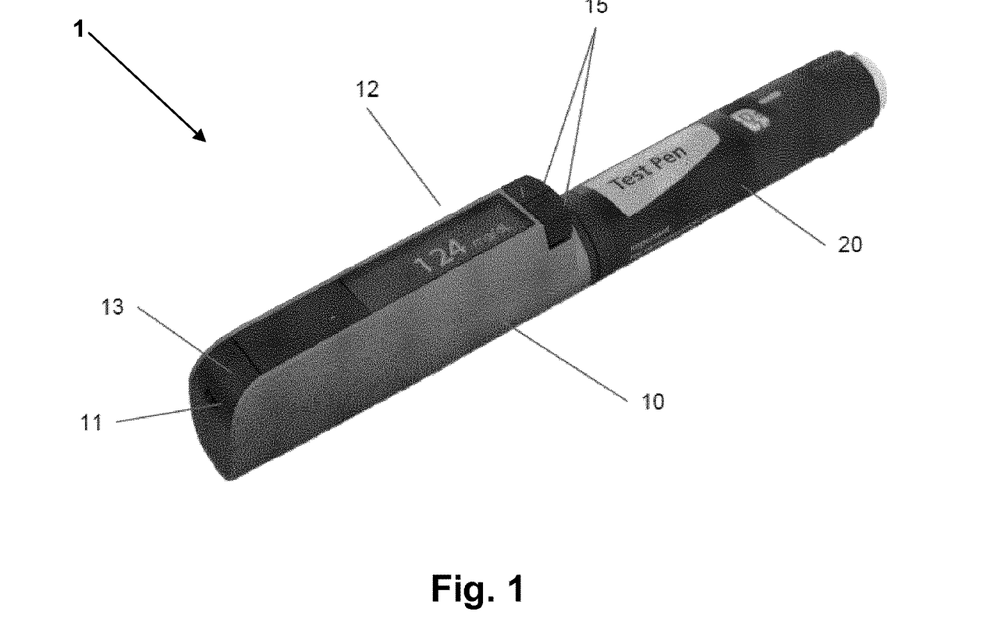
FIG. 1 shows a drug delivery device in combination with a mounted cap device.

FIG. 1 shows a drug delivery assembly 1 comprising a drug delivery device 20 containing an insulin formulation and onto which is mounted a cap device 10. The cap comprises a strip port for a BGM arranged in the interior of the cap, a display 12 adapted to show BG values as well as other values (e.g. a LCD or OLED), an input button 13 adapted to confirm a given value, e.g. a BG reading, as well as a set of up/down buttons 15 adapted to scroll in a given log, e.g. a BG log. The cap further comprises means for detecting when it has been removed from the drug delivery device as well as a port for uploading data to an external device (not shown).

The shown cap further comprises processor and memory means for calculating a recommended change in drug delivery. For example, if the cap was adapted to support a patient during initial titration in a once-daily injection regimen with a long-acting insulin such as Levemir® from Novo Nordisk in combination with oral anti-diabetic agents, then the cap device may be loaded with a simple algorithm corresponding the above-described titration guideline for Levemir®. For example, if the average of the 5 last BG measurements was 8.5 mmol/L the cap would recommend adjusting the Levemir® dose with +4 units. The recommendation could be prompted and display in several ways. For example, the user may have to prompt the device to display the recommendation by using the input button in a specified way. As the titration dose regimen is based on fasting BG and bed-time injection of insulin, removing the cap from the drug delivery device may also be used to prompt the cap. The recommendation could be shown as "+4 total 24 units" this indicating both the change in dosing and the total amount of insulin to inject.

According to an aspect of the invention the cap device 10 is provided with additional means for assuring safe titration. More specifically, the processor is further programmed to calculate a correction value for BG values determined at a plurality of times, this allowing the calculated variation of the component to be reduced as a function of the calculated correction value. In other words a safety factor has been incorporated.

For example, a basic titration algorithm could be expressed as:

$$IU_{Titration\ level}(n) = IU_{Titration\ level}(n-1) + \text{Babystep}(n) \quad (1)$$

$$\text{Babystep}(n) = ISF_{average}(n) * (\text{Average}_{FBG}(n) - \text{Target}_{FBG}) * SF(FBG_{Variance}) \quad (2)$$

Wherein:
$IU_{Titration\ level}(n)$=New insulin titration dose [IU]
$\text{Target}_{FBG}$=Target Fasting BG level [mmol/L]

The safety factor value $SF(FBG_{Variance})$ is a value in the range 1-0, wherein the value is 1 when the $FBG_{Variance}$ is minimal and thus fully acceptable and 0 when the $FBG_{Variance}$ is very large and thus fully unacceptable. The exact correlation between $FBG_{Variance}$ and the safety factor value will depend on factors such as the type of insulin, the type of patient, and the preferences of the medial professional responsible for the initialisation process.

$$ISF_{average}(n) = \text{The average } ISF \text{ over the previous period } [IU/mmol/L] = (ISF(n-1) + ISF(n-2) \ldots ISF(n-m))/m \quad (3)$$

$$ISF(n-1) = IU_{Titration\ level}(n-1) - IU_{Titration\ level}(n-2))/((\text{Average}_{FBG}(n-1) - \text{Average}_{FBG}(n-2))) \quad (4)$$

$$\text{Average}_{FBG}(n) = \text{Average Fasting } BG \text{ over the last days } [n, n-1 \ldots n-m]. \quad (5)$$

In case the cap device as in the FIG. 1 embodiment is provided with means for registering compliance (here: cap-off detection), a second safety factor value could incorporate compliance data and thus be determined as SF(Compliance). For example, if the patient is fully within compliance, e.g. all injections are considered to be taken in accordance with the regimen, the factor is 1. In contrast, if all injections were taken at the wrong time of the day (or not taken at all), the factor is 0.5. Indeed, a much more elaborate SF(Compliance) function could be used.

To further improve safety BG measurements could be categorized in categories relevant to the algorithm. In a simple form this categorisation could be either "fasting" or "non-fasting" BG, or could further include "pre-prandial" and "postprandial" BG. The categorisation could be done automatically based on time and value of measurement or manually by input from the user or a combination.

Further, incorporating supervision or safety logic into the titration algorithm could further improve safety. The patterns recognised by supervision could be: identification of abnormal variation in BG, abnormal gradients in BG (rapid increase or decrease), no response to dose change, too high fasting BG values, too low fasting BG values (hypoglycaemia), too high/low prandial BG values. Another example of a supervising element could be to limit the selftitration algorithm to a certain step size. If the supervision detects problems in the titration it could warn the user to call or visit a physician or the system could send a warning directly to the physician using wireless technologies.

As the patient uses the cap device 10 logs are created storing logs of (accepted) BG values, dose size recommendations as well as cap-off events. The log may be based on either real or relative time. In the latter case the relative time stamps would be provided with absolute time stamps when transferred to an external device.

Figure 2:
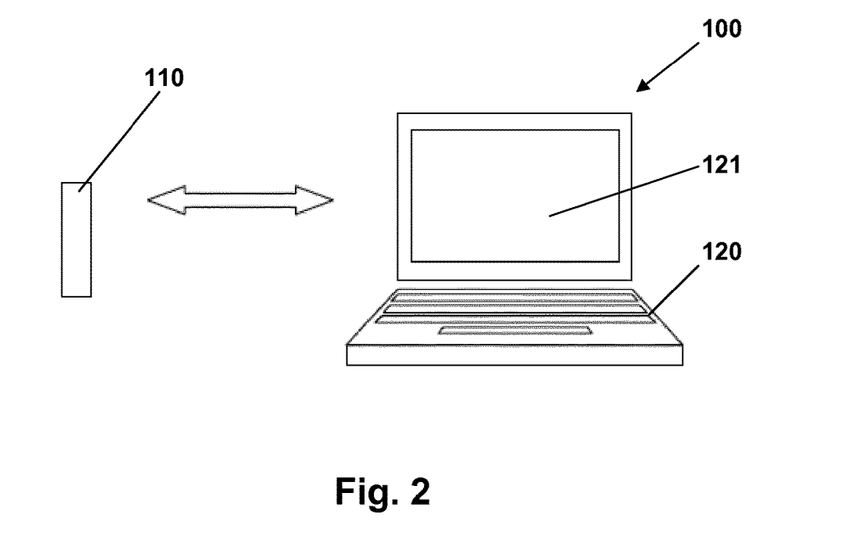
FIG. 2 shows a system for displaying information.

FIG. 2 shows a system 100 for optimizing a patient's basal insulin dosage regimen over time, and comprising a patient unit 110 and a display unit 120. The patient unit is in the form of a BGM cap device of the type shown in FIG. 1 and the display unit is in the form of a laptop computer. The shown units are adapted for wireless and bi-directional communication by e.g. RF such as Bluetooth, NFC or IR. Communication may be initiated by either device. Alternative communication may be by wire. When a patient is initiated on e.g. Levemir® patient specific parameters are uploaded to the cap device. Depending on how advanced the titration algorithm is more or less information will be needed, e.g. for a simple algorithm as described above the initial daily administration of a single dose of 10 U will be entered. As the patient uses the BGM cap BG and recommended dose data will be logged in the memory for subsequent upload to the PC when the patient comes to visit the doctor's office.

Figure 3:
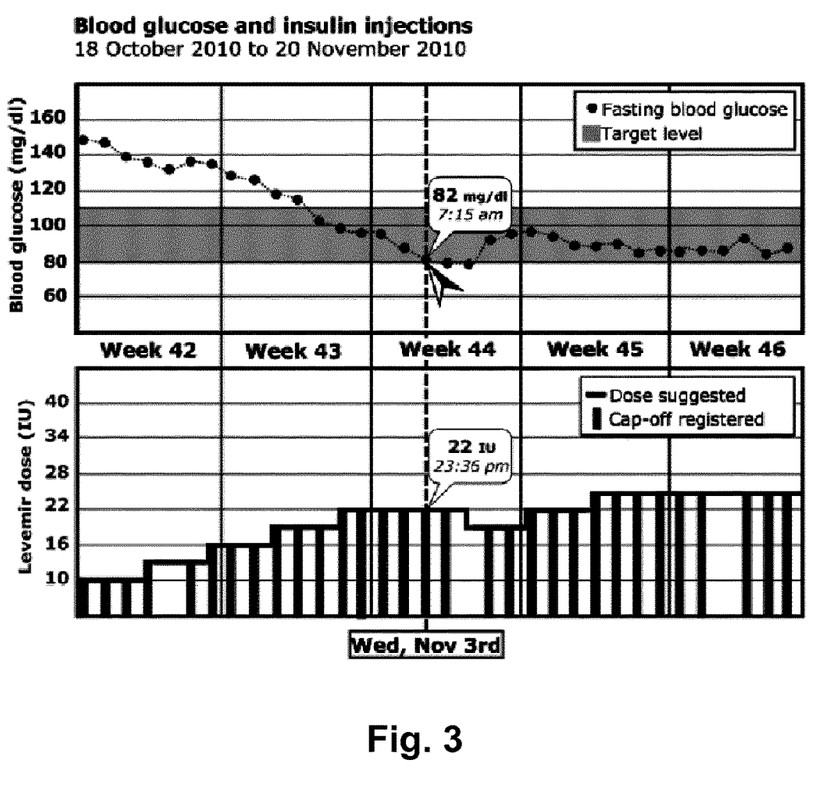
FIG. 3 shows graphs displaying patient information as a function of time.

When the log data is uploaded to an external device such as a doctors' PC, the data may be displayed as shown in FIG. 3. As can be seen, the PC is provided with software presenting the BG values, recommendations and cap-off events as a function of time, each logged event being provided with an absolute time stamp. In this way a comprehensive overview is provided which can help the doctor evaluate the patient's titration regimen just as it provides the background for the calculated safety factors. The software is further adapted to provide statistic data and statistical analyses to further assist the doctor. Indeed, the same information could be uploaded to the patient's PC or to a smartphone.

Figure 4:
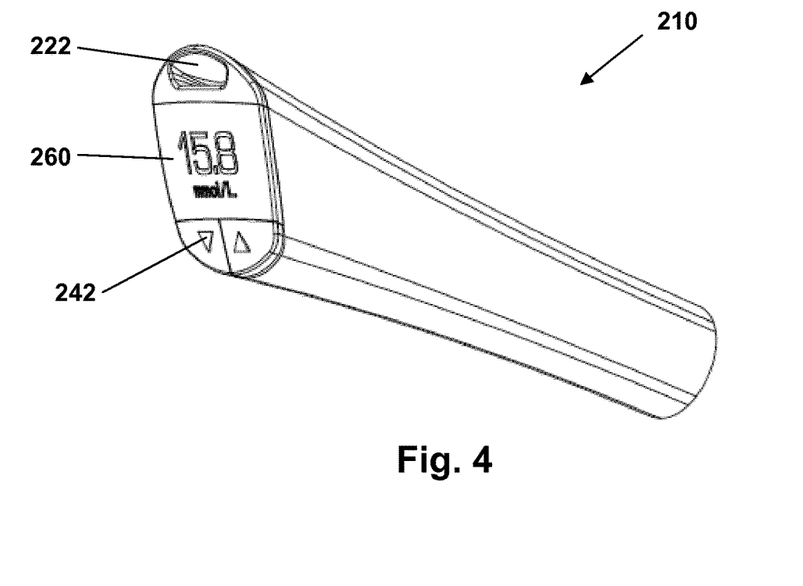
FIG. 4 shows a further cap device.
Figure 5:
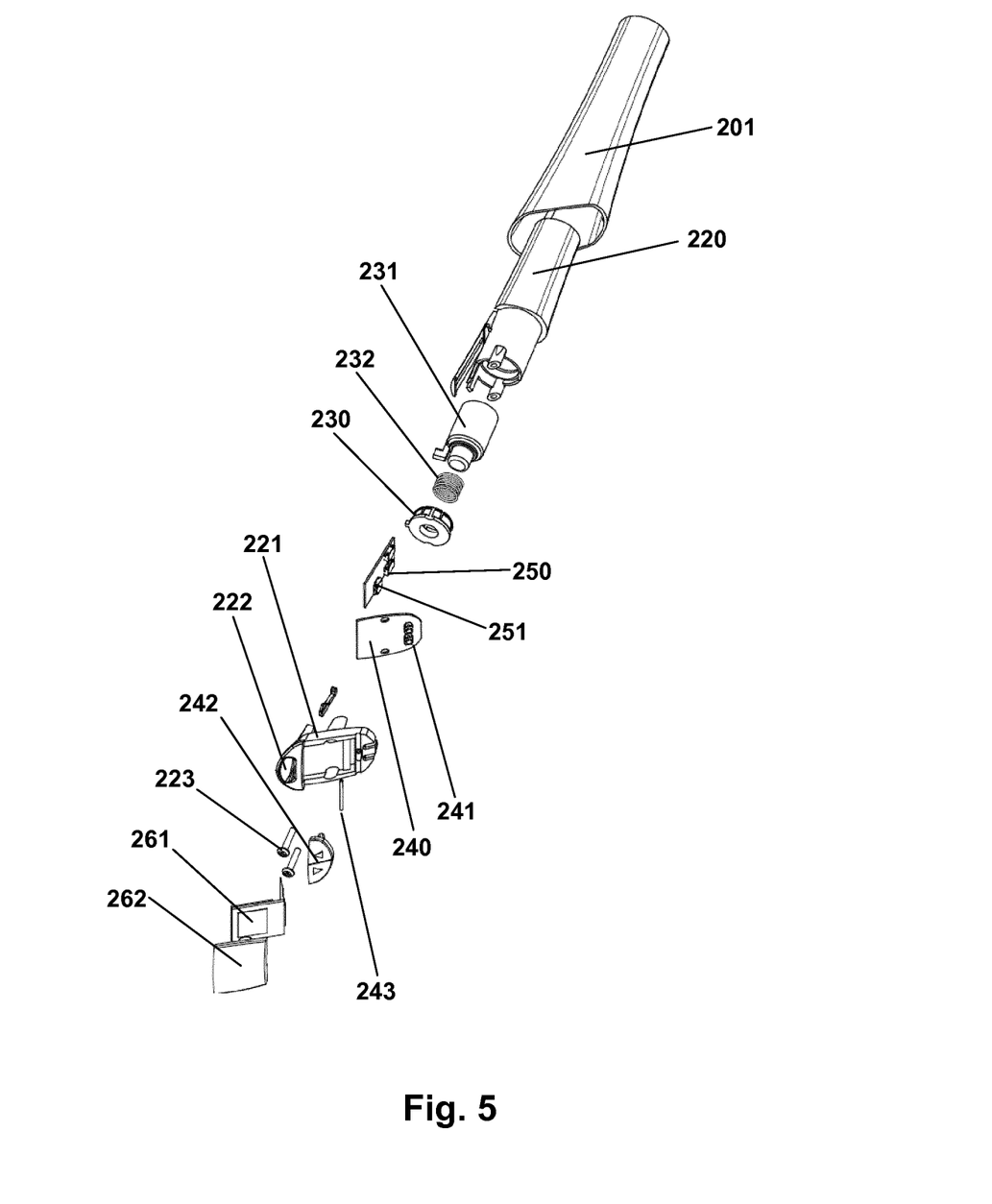
FIG. 5 shows an exploded view of the cap device of FIG. 4.

FIG. 4 shows an alternative configuration of a BGM cap 210 in which a strip port 222, a display 260 and user buttons 242 are arranged at the distal end of the cap. As seen in FIG. 5 the cap comprises a housing member 201 in which a generally tubular main chassis 220 is arranged, the latter having a top chassis 221 with a strip port 222 attached by screws 223. A spring support member 230 is attached to the main chassis. An actuator cup 231 is slidingly received in the main chassis in which it can travel between an un-loaded and a loaded position, the cup being biased towards its initial position by a spring 232 arranged between the spring support and the distal end of the cup, the cup being adapted to be moved distally when the cap is mounted on the distal end of a corresponding drug delivery device as seen in FIG. 1. The cap further comprises a first PCB 240 on which button switches 241 as well as an energy source and controller, memory and transmission means (not shown) are arranged, and a second PCB 250 on which cup-actuated switch means 251 and a BGM unit (not shown) are arranged. The switch means 251 is actuated when the cup 231 is moved axially thereby detecting a cap-off event. A display 261 is connected to the first PCB and covered by a transparent window member 262 attached to the top chassis to which further is attached two buttons 242 by means of an axel 243 allowing the buttons to pivot.

Figure 6:
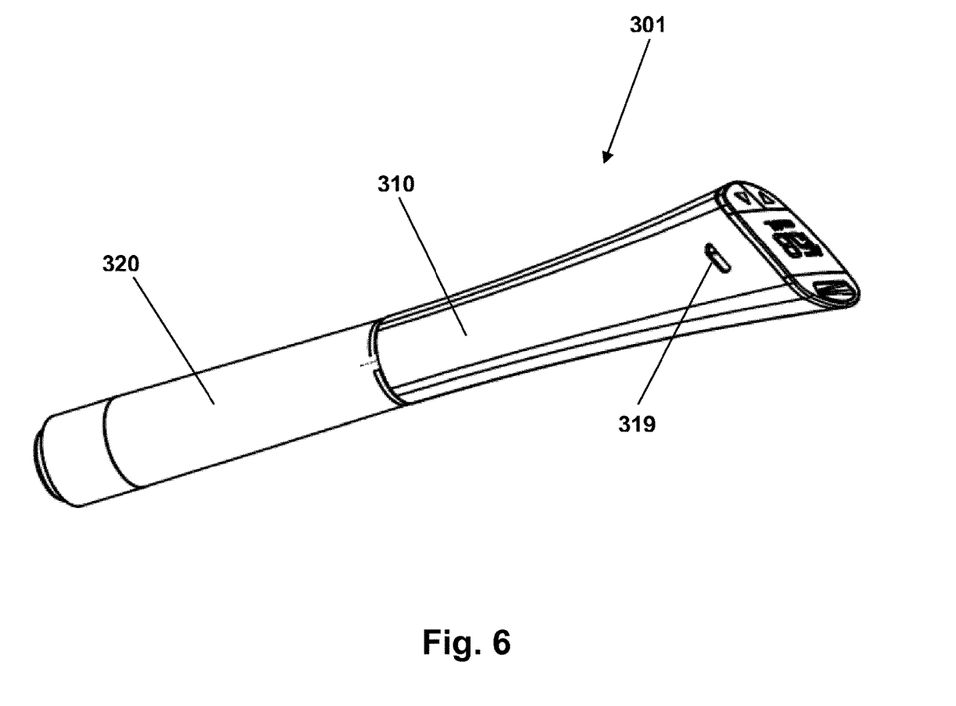
FIG. 6 shows a further cap device mounted on a drug delivery device.

FIG. 6 shows a drug delivery assembly 301 comprising a drug delivery device 320 of the type shown in FIG. 1 and onto which is mounted a cap device 310. The cap device is similar to the BGM cap device of FIG. 4, however, instead of wireless communication means the cap device is provided with an I/O port 319 adapted for wired communication.

In the shown embodiment of FIG. 1 the drug delivery device is a pre-filled pen device intended for single use only, however, the pen could also be a durable device intended to be used with exchangeable drug cartridges. In case the pen is of the durable type it may be provided with electronic means for detecting and creating a dose log which then could be transmitted to the cap device 10.

Figure 7:
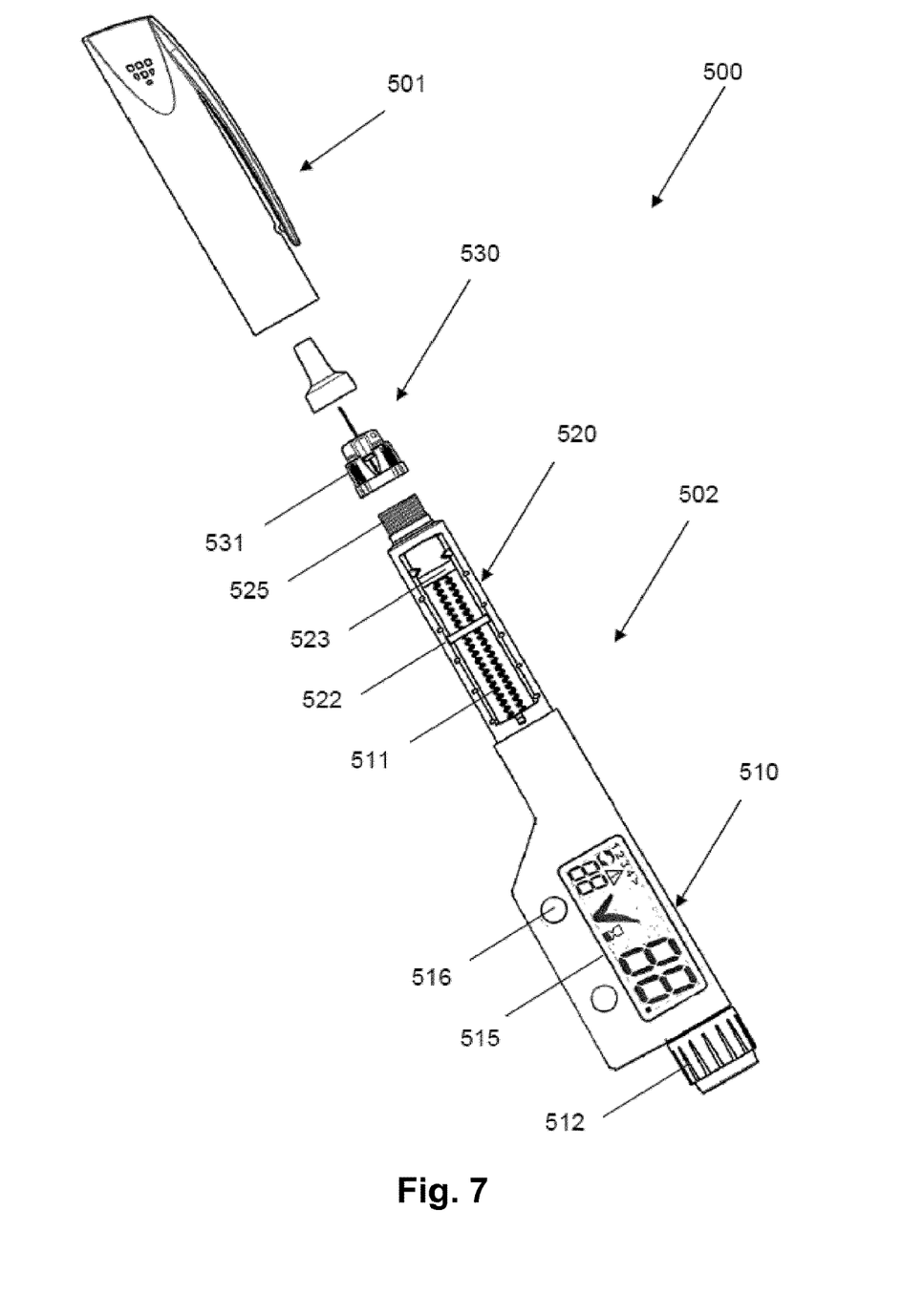
FIG. 7 shows a drug delivery means comprising electronic logging and display means.

FIG. 7 shows such a pen 500. The pen device comprises a cap portion 501 (here shown as a normal cap not related to the cap device 10) and a main portion 502 having a proximal part 510 in which a drug expelling mechanism is arranged, and a distal reservoir part 520 in which a replaceable drug-filled transparent cartridge 521 with a distal needle-penetratable septum is arranged and hold in place by a cartridge holder 522 releasably mounted to the proximal part, the cartridge holder having openings allowing a portion of the cartridge to be inspected. The cartridge is provided with a piston 523 driven by a piston rod 511 forming part of the expelling mechanism, the piston rod being adapted to be pushed back when a new cartridge is mounted. A proximal-most button 512 serves to manually set and expel a desired dose of drug. This type of a mechanical pen-formed drug delivery device is well known, see e.g. WO 99/38554 to which reference is made for further details in respect of the internal construction of the shown type of pen. The cartridge (or alternatively the cartridge holder) is provided with distal coupling means in the form of a hub mount 525 having, in the shown example, an external thread adapted to engage an inner thread of a hub 531 of a needle assembly 530. The proximal part further comprises a display 515, user actuatable keys 516 as well as electronic means (not shown) for detecting and storing information representing operations performed by the expelling mechanism. The detection means for detecting a set and/or expelled dose may be adapted to detect directly or indirectly the position of the piston rod, see e.g. U.S. Pat. No. 6,585,698 which is hereby incorporated by reference. The electronic means is adapted to store data representing injections performed by the user in the form of a time and dose log. The display may show the actual dose being set by a user using the button 512, the last dose (e.g. amounts of units expelled) and the time since last dose (or the actual time for the last dose), or the user may use the keys 516 to scroll through the log to display previous expelling data. The pen is adapted to transmit data to another system or device, which in the present context would be the cap device 10 of FIG. 1.

In the above description of the preferred embodiment, the different structures and means providing the described functionality for the different components have been described to a degree to which the concept of the present invention will be apparent to the skilled reader. For example, with reference to FIG. 5 a cap comprising switch means adapted to be actuated by axial movement when the cap is mounted on the distal end of a corresponding drug delivery device, however, in EP application 11165063.6 an alternative design is disclosed in which mounting of a cap onto (or de-mounting from) a corresponding drug delivery device is detected by radial movement of a switch. The detailed construction and specification for the different components are considered the object of a normal design procedure performed by the skilled person along the lines set out in the present specification.

The invention claimed is:

1. A drug delivery assembly comprising:
   (i) a memory structure adapted to receive data representing an initial basal insulin dosage regimen and fasting blood glucose values as a function of time over a period from m to n, wherein each of m and n is an integer representing a number of days;
   (ii) a processor operatively connected to the memory structure and programmed to perform a titration process to obtain a new insulin titration dose;
   wherein $$IU_{Titration\ level}(n) = IU_{Titration\ level}(n-1) + \text{Babystep}(n);$$

wherein $$\text{Babystep}(n) = ISF_{average}(n) * (\text{Average}_{FBG}(n) - \text{Target}_{FBG}) * SF(FBG_{Variance});\text{ and}$$

wherein
   $IU_{Titration\ level}(n)$ is the new insulin titration dose,
   $IU_{Titration\ level}(n-1)$ is a previous insulin titration dose,
   $ISF_{average}(n)$ is an average insulin sensitivity factor over the period from n−1 to n−m,
   $\text{Average}_{FBG}(n)$ is an average fasting blood glucose over the period from n to n−m,
   $\text{Target}_{FBG}$ is a target fasting blood glucose level, and
   $SF(FBG_{Variance})$ is a safety factor value that is a function of the variance of the fasting blood glucose, wherein the value is in the range of 0 to 1; and
   (iii) an output structure adapted to communicate to the patient the new insulin titration dose;
   (iv) an insulin reservoir or structure adapted to receive an insulin reservoir;
   (v) an outlet for the insulin; and
   (vi) an insulin expelling mechanism adapted to expel the new titration insulin dose from the reservoir and out through the device.

2. The drug delivery assembly according to claim 1, further comprising:
   a blood glucose meter structured to receive a patient blood sample and generate fasting blood glucose values as a function of time from patient blood samples; and
   a transmission structure adapted to transmit the fasting blood glucose values as a function time to the memory structure.

3. The drug delivery assembly according to claim 1, further comprising:
   a detection structure adapted to detect when a patient-actuated operation is performed, wherein the operation is indicative of the administration of a dose of an insulin containing drug; wherein
   the memory structure is further is adapted to receive data representing detected patient-actuated operations as a function of time, and
   the processor is further programmed to calculate a compliance value based on the detected patient-actuated operations compared to a pre-defined schedule for the patient-actuated operations.

4. The drug delivery assembly according to claim 3, wherein the detection structure is adapted to detect a cap-off event when the cap has been at least partially de-mounted from the drug delivery device for a pre-determined amount of time.

5. The drug device assembly according to claim 3, wherein
   the detection structure is adapted to detect, store, and transmit dose data representing the size of an expelled dose,
   and wherein the drug device assembly further comprises a receiving structure adapted to receive the transmitted dose data.

6. The drug delivery assembly according to claim 3, wherein the detection structure is adapted to detect when the drug expelling mechanism has been actuated.

7. The drug delivery assembly according to claim 1, wherein the processor is further adapted to disregard a blood glucose value if the given blood glucose value corresponds to a blood glucose value outside a predefined range.

8. A drug delivery assembly comprising:
   (i) a memory structure adapted to receive data representing an initial basal insulin dosage regimen and fasting blood glucose values as a function of time over a period from m to n, wherein each of m and n is an integer representing a number of days;
   (ii) a processor operatively connected to the memory structure and programmed to perform a titration process to obtain a new insulin titration dose;
   wherein $$IU_{Titration\ level}(n) = IU_{Titration\ level}(n-1) + \text{Babystep}(n);$$

wherein $$\text{Babystep}(n) = ISF_{average}(n) * (\text{Average}_{FBG}(n) - \text{Target}_{FBG}) * SF(FBG_{Variance});\text{ and}$$

wherein
   $IU_{Titration\ level}(n)$ is the new insulin titration dose,
   $IU_{Titration\ level}(n-1)$ is a previous insulin titration dose,
   $ISF_{average}(n)$ is an average insulin sensitivity factor over the period from n−1 to n−m,
   $\text{Average}_{FBG}(n)$ is an average fasting blood glucose over the period from n to n−m,
   $\text{Target}_{FBG}$ is a target fasting blood glucose level, and
   $SF(FBG_{Variance})$ is a safety factor value that is a function of the variance of the fasting blood glucose, wherein the value is in the range of 0 to 1; and
   (iii) an output structure adapted to communicate to the patient the new insulin titration dose;
   (iv) an insulin reservoir or structure adapted to receive an insulin reservoir;
   (v) an outlet for the insulin;
   (vi) an insulin expelling mechanism adapted to expel the new titration insulin dose from the reservoir and out through the device; and
   (vii) a detection structure adapted to detect when a patient-actuated operation is performed, wherein the operation is indicative of the administration of a dose of an insulin containing drug and is selected from the group consisting of:
   a cap-off event when the cap has been at least partially de-mounted from the drug delivery device for a pre-determined amount of time,
   the size of an expelled dose, and
   when the drug expelling mechanism has been actuated;
   wherein the memory structure is further is adapted to receive data representing detected patient-actuated operations as a function of time; and wherein the processor is further programmed to calculate a compliance value based on the detected patient-actuated operations compared to a pre-defined schedule for the patient-actuated operations.

9. The drug delivery assembly according to claim 8, wherein the patient-actuated operation is a cap-off event when the cap has been at least partially de-mounted from the drug delivery device for a pre-determined amount of.

10. The drug device assembly according to claim 8, wherein the patient-actuated operation is the size of an expelled dose.

11. The drug delivery assembly according to claim 8, wherein the patient-actuated operation is when the drug expelling mechanism has been actuated.

12. The drug delivery assembly according to claim 8, further comprising:
- a blood glucose meter structured to receive a patient blood sample and generate fasting blood glucose values as a function of time from patient blood samples; and
- a transmission structure adapted to transmit the fasting blood glucose values as a function of time to the memory structure.

\* \* \* \* \*